United States Patent
Fontaine

(10) Patent No.: US 12,000,404 B1
(45) Date of Patent: Jun. 4, 2024

(54) INRUNNER AXIAL COMPRESSOR

(71) Applicant: ZeroAvia, Inc., Hollister, CA (US)

(72) Inventor: Jonathan Leopold Nutzati Fontaine, Hollister, CA (US)

(73) Assignee: ZEROAVIA, INC., Hollister, CA (US)

( * ) Notice: Subject to any disclaimer, the term of this patent is extended or adjusted under 35 U.S.C. 154(b) by 0 days.

(21) Appl. No.: 18/458,787

(22) Filed: Aug. 30, 2023

(51) Int. Cl.
*F04D 25/06* (2006.01)
*F04D 29/58* (2006.01)
*H01M 8/04111* (2016.01)

(52) U.S. Cl.
CPC ......... *F04D 25/06* (2013.01); *F04D 29/5806* (2013.01); *H01M 8/04111* (2013.01); *H01M 2250/20* (2013.01)

(58) Field of Classification Search
CPC ... H01M 8/04111; F01D 15/10; H02K 7/1823
See application file for complete search history.

(56) References Cited

U.S. PATENT DOCUMENTS

| | | | |
|---|---|---|---|
| 3,801,372 A | 4/1974 | Shaw | 429/431 |
| 5,106,035 A | 4/1992 | Langford | B64D 27/24 |
| 5,810,284 A | 9/1998 | Hibbs et al. | B64C 39/10 |
| 6,119,979 A | 9/2000 | Lee et al. | B64B 1/44 |
| 6,296,957 B1 | 10/2001 | Graage | H01M 8/09 |
| 6,322,915 B1 | 11/2001 | Collins et al. | H01M 8/04 |
| 6,380,637 B1 | 4/2002 | Hsu | B60L 58/34 |
| 6,568,633 B2 | 5/2003 | Dunn | B64D 27/24 |
| 2001/0018138 A1 | 8/2001 | Iwase | B60L 11/18 |
| 2002/0005454 A1 | 1/2002 | MacCready et al. | |
| 2003/0096148 A1 | 5/2003 | Edwards | H01M 8/2432 |
| 2004/0043267 A1 | 3/2004 | Schuler | H01M 8/2432 |
| 2004/0228055 A1 | 11/2004 | Pearson | |
| 2006/0093883 A1 | 5/2006 | Pristash | H01M 8/04291 |
| 2006/0222485 A1* | 10/2006 | Lardellier | F01D 9/065 415/115 |

(Continued)

FOREIGN PATENT DOCUMENTS

| | | | | |
|---|---|---|---|---|
| DE | 19821952 | | 11/1999 | B64D 41/00 |
| EP | 2280150 A1 * | | 2/2011 | F01D 15/10 |

(Continued)

OTHER PUBLICATIONS

Cui, Zhiheng, Jiangjiang Wang, and Noam Lior. 2021. "Thermodynamic Analysis of a Solid Oxide Fuel Cell Based Combined Cooling, Heating, and Power System Integrated with Biomass Gasification" *Entropy* 23, No. 8: 1029. https://doi.org/10.3390/e23081029.

(Continued)

*Primary Examiner* — Kenneth J Hansen
(74) *Attorney, Agent, or Firm* — HAYES SOLOWAY P.C.

(57) ABSTRACT

A fuel-cell-powered vehicle includes an electrically-powered turbine assembly having a housing, a rotating shaft, an air compressor comprising a compressor stator fixed to the housing and a compressor rotor fixed to the rotating shaft, an electric motor including an electric motor stator fixed to the compressor stator and an electric motor rotor fixed to the rotating shaft, a turbine including a turbine stator affixed to the housing, a turbine rotor fixed to the rotating shaft, and two or more fuel cells arranged around an outside of the electrically-powered turbine assembly.

20 Claims, 3 Drawing Sheets

(56) References Cited

U.S. PATENT DOCUMENTS

| | | | |
|---|---|---|---|
| 2008/0145716 A1 | 6/2008 | Yu | |
| 2009/0212634 A1 | 8/2009 | Kojima | |
| 2012/0189875 A1 | 7/2012 | Fischel | ............... B01J 14/005 |
| 2015/0357658 A1 | 12/2015 | Kashyap | ............. H01M 8/2457 |
| 2016/0181641 A1 | 6/2016 | Hoffjann | ............. H01M 8/1007 |
| 2017/0175565 A1 | 6/2017 | Sennoun | ................. F02C 6/10 |
| 2017/0211474 A1 | 7/2017 | Sennoun | ................. F02C 6/00 |
| 2018/0223739 A1* | 8/2018 | Dubreuil | ............. F04D 29/321 |
| 2018/0304753 A1 | 10/2018 | Vondrell | ................ B64C 21/06 |
| 2021/0151783 A1* | 5/2021 | Miftakhov | ........ H01M 8/04738 |
| 2021/0324802 A1* | 10/2021 | Bonnoitt | ................ F01D 15/10 |
| 2022/0325666 A1 | 10/2022 | Miftakhov et al. | ....... F02C 7/12 |

FOREIGN PATENT DOCUMENTS

| | | | | |
|---|---|---|---|---|
| EP | 2878795 | 6/2015 | ............ | B64D 27/24 |
| EP | 3199791 | 8/2017 | ............... | F02C 6/00 |
| JP | 201917792 | 7/2019 | ............. | H01M 8/00 |
| WO | WO2022056107 | 3/2022 | ............... | F02K 5/00 |

OTHER PUBLICATIONS

Extended European Search Report for Application No. 20208430.7 dated Apr. 13, 2021, 11 pages.

Fernandes, M. D., et al. "SOFC-APU systems for aircraft: A review." International Journal of Hydrogen Energy 43.33 (2018): 16311-16333 (Year: 2018).

General Electric Aviation, "The Single-Spool Core: A proven design for performance and simplicity", t901-white-paper.pdf, retrieved Oct. 19, 2023, 6 pages, https://web.archive.org/web/20170630095803/https://www.geaviation.com/sites/defaultlfiles/single-vs-dual-spool.pdf ( Year: 2017).

Petrescu, Reily Victoria, et al. "Modern propulsions for aerospace—a review." Journal of Aircraft and Spacecraft Technology 1.1 (2017) (Year: 2017), 41 pages.

Search Report, Written Opinion and International Preliminary Report for Patentability issued in International Application No. PCT/US21/49635, 23 pages, dated Dec. 13, 2021.

Song, et al, Performance analysis of a tubular solid oxide fuel cell/micro gas turbine hybrid power system based on a quasi-two dimensional model, Journal of Power Sources, vol. 142, Issues 1-2, 2005, pp. 30-42, ISSN 0378-7753, https://doi.org/10.1016/j.jpowsour.2004.10.011. (https://www.sciencedirect.com/science/article/pii/S0378775304010845).

Thomas, Sharon and Zalbowitz, Marcia, "Fuel Cells-Green Power", Los Alamos National Laboratory, The 3M Foundation, 36 pages, 2006.

U.S. Appl. No. 63/532,871, filed Aug. 15, 2023.

Zhixing Ji, et al, Comparative performance analysis of solid oxide fuel cell turbine-less jet engines for electric propulsion airplanes: Application of alternative fuel, Aerospace Science and Technology, vol. 93, 2019, 105286, ISSN 1270-9638, https://doi.org/10.1016/j.ast.2019.07.019. (https://www.sciencedirect.com/science/article/pii/S1270963819311174).

* cited by examiner

Fig. 1 - Prior Art

INRUNNER AXIAL COMPRESSOR

TECHNICAL FIELD

The present disclosure relates to hydrogen fuel cell electric engine systems for use with vehicles such as aircraft and will be described in connection with such utility, although other utilities are contemplated.

BACKGROUND AND SUMMARY

This section provides background information related to the present disclosure which is not necessarily prior art. This section provides a general summary of the disclosure and is not a comprehensive disclosure of its full scope or all its features.

Exhaust emissions from transport vehicles are a significant contributor to climate change. Conventional fossil-fuel-powered aircraft engines release $CO_2$ emissions. Also, fossil-fuel-powered aircraft emissions include non-$CO_2$ effects due to nitrogen oxide (NOx), vapor trails, and cloud formation triggered by the altitude at which aircraft operate. These non-$CO_2$ effects are believed to contribute twice as much to global warming as aircraft $CO_2$ and are estimated to be responsible for two-thirds of aviation's climate impact. Additionally, the high-speed exhaust gasses of conventional fossil-fuel-powered aircraft engines contribute significantly to the extremely large noise footprint of commercial and military aircraft, particularly in densely populated areas.

Rechargeable battery-powered terrestrial vehicles, i.e., "EVs", are slowly replacing conventional fossil-fuel-powered terrestrial vehicles. However, the weight and limited energy storage of batteries makes rechargeable battery-powered aircraft generally impractical.

Hydrogen fuel cells offer an attractive alternative to fossil-fuel-burning engines. Hydrogen fuel cell tanks may be quickly filled and store significant energy, and other than the relatively small amount of unreacted hydrogen gas, the reaction output exhausted from hydrogen fuel cells comprises essentially only water.

In our prior US Published Application No. US 2021/0151783 (hereinafter '783 application), we describe an integrated hydrogen fuel-cell-powered electric engine system that can be utilized, for example, in a turboprop or turbofan system, to provide a streamlined, light weight, power dense and efficient system. Referring to FIG. 1, the integrated hydrogen-electric engine system 1 of our prior '783 application includes an elongated shaft 10 that defines a longitudinal axis "L" and extends through the entire powertrain of integrated hydrogen-electric engine system 1 to function as a common shaft for the various components of the powertrain. Elongated shaft 10 supports propulsor 14 (e.g., a fan or propeller), a multi-stage air compressor system 12, 12a, 12b, a fuel pump 22 in fluid communication with a fuel source 20 (e.g., liquid hydrogen—$LH_2$), a heat exchanger 24 in fluid communication with air compressor system 12, 12a, 12b, a fuel cell stack 26 in fluid communication with heat exchanger 24, and a motor assembly 30 disposed in electrical communication with inverter 29 and fuel cell stack 26.

Air compressor system 12, 12a, 12b of integrated hydrogen-electric engine system 1 includes an air inlet portion 12a at a distal end thereof and a compressor portion 12b that is disposed proximally of air inlet portion 12a for uninterrupted, axial delivery of airflow in the proximal direction. Compressor portion 12b supports a plurality of longitudinally spaced-apart rotatable compressor wheels 16 (e.g., multi-stage) that rotate in response to rotation of elongated shaft 10 for compressing air received through air inlet portion 12a for pushing the compressed air to a fuel cell stack 26 for conversion to electrical energy. As can be appreciated, the number of compressor wheels/stages 16 and/or diameter, longitudinal spacing, and/or configuration thereof can be modified as desired to change the amount of air supply, and the higher the power, the bigger the propulsor 14. These compressor wheels 16 can be implemented as axial or centrifugal compressor stages. Further, the compressor can have one or more bypass valves and/or wastegates 17 to regulate the pressure and flow of the air that enters the downstream fuel cell, as well as to manage the cold air supply to any auxiliary heat exchangers in the system.

Compressor 12b optionally can be mechanically coupled to elongated shaft 10 via a gearbox 18 to change (increase and/or decrease) compressor turbine rotations per minute (RPM) and to change airflow to fuel cell stack 26. For instance, gearbox 18 can be configured to enable the airflow, or portions thereof, to be exhausted for controlling a rate of airflow through the fuel cell stack 26, and thus, the output power.

Integrated hydrogen-electric engine system 1 further includes a gas management system such as a heat exchanger 24 disposed concentrically about elongated shaft 10 and configured to control thermal and/or humidity characteristics of the compressed air from air compressor system 12 for conditioning the compressed air before entering fuel cell stack 26. Integrated hydrogen-electric engine system 1 further also includes a fuel source 20 of cryogenic fuel (e.g., liquid hydrogen—$LH_2$, or cold hydrogen gas) that is operatively coupled to heat exchanger 24 via a pump 22 configured to pump the fuel from fuel source 20 to heat exchanger 24 for conditioning. In particular, the $LH_2$ fuel, while in the heat exchanger 24, becomes gasified (e.g., $LH_2$ converts to hydrogen gas—$H_2$) due to heat absorbed from the compressed air. The hydrogen gas is then further heated in the heat exchanger 24 to a working temperature of the fuel cell 26 which also cools the compressed air to a working temperature of the fuel cell 26. In one embodiment, a heater 39 can be coupled to or included with heat exchanger 24 to increase heat as necessary, for instance, when running under a low power regime. Integrated hydrogen-electric engine system 1 also may include one or more external radiator(s) 19 for facilitating airflow and adding, for instance, additional cooling. Additionally, and/or alternatively, motor assembly 30 can be coupled to heat exchanger 24 for looping in the cooling/heating loops from motor assembly 30 as necessary. Such heating/cooling control can be managed, for instance, via controller 200 of integrated hydrogen-electric engine system 1. In one embodiment, fuel source 20 can be disposed in fluid communication with motor assembly 30 or any other suitable component to facilitate cooling of such components.

Pump 22 can be coaxially supported on elongated shaft 10 for actuation thereof in response to rotation of elongated shaft 10. Heat exchanger 24 is configured to cool the compressed air received from air compressor system 12, 12a, 12b with the assistance of the pumped liquid hydrogen.

While existing hydrogen fuel-cell-powered electric engine systems such as disclosed in our prior '783 application, and as illustrated in FIG. 1, discussed above, advantageously may be mounted in the nose of an aircraft, such hydrogen fuel-cell-powered engine systems are too large and awkwardly shaped for packaging in conventional aircraft wing nacelles. As a result, conventional hydrogen fuel cell electric engine architectures do not provide sufficient power density to replace conventional fossil-fuel-powered turbine engines.

In our co-pending U.S. Application Ser. No. 63/532,871 filed Aug. 15, 2023, the contents of which are incorporated herein by reference, we describe a compact hydrogen fuel cell electric engine system comprising a centrifugal compressor and a turbine assembly rotatably mounted back-to-back on a common shaft, having one or more fuel cells mounted outside of the rotated mounted centrifugal compressor and rotatably mounted turbine assembly. The present disclosure provides a hydrogen fuel cell electric system having an even more compact architecture.

More particularly, the subject disclosure provides a compact electrically-powered turbine assembly in which an electric motor, an air compressor system, and a turbine system are arranged around a central rotating shaft, in a housing. The compressor stators and the turbine stators are affixed to the housing, and the electric motor stators are affixed to the compressor stators. The compressor blades and turbine blades, and the electric motor cores are all affixed to the rotating shaft, and the electric motors are located within the compressor system and the turbine system. One or more fuel cells and inverters are arranged to the exterior of the housing resulting in an extremely compact system that can be fitted into a conventional fossil-fuel-powered aircraft nacelle. This permits us to retrofit conventional fossil-fuel-powered aircraft, replacing the existing fossil-fuel-powered turbine engines with hydrogen fuel cell electric engines.

In accordance with Aspect A of the present disclosure, we provide an electrically-powered turbine assembly comprising: a housing; a rotating shaft; an air compressor comprising a compressor stator fixed to the housing and a rotor fixed to the rotating shaft; an electric motor including an electric motor stator fixed to the compressor stator and core fixed to the rotating shaft; and a turbine including a turbine stator fixed to the housing and a rotor fixed to the rotating shaft.

In one embodiment, an electric motor or generator is affixed to the turbine stator, and a turbine rotor is fixed to the motor or generator rotor.

In another embodiment, the electric motor core, the compressor rotor, and the turbine rotor are mechanically linked together via the rotating shaft.

In another embodiment, one or more of the compressor stator and/or the electric motor stator and/or the turbine stator is/are configured for carrying an electric current.

In one embodiment, one or more of the compressor stators and/or the turbine stators and/or the electric motor stators has/have a passage or passages configured to accommodate an electrical conduit within the stator. In another embodiment the one or more of the compressor stators and/or the turbine stators preferably is/are formed of an electrically conductive material and is configured to carry an electrical current.

In another embodiment, one or more of the compressor stators and/or turbine stators and/or the electric motor stators has/have a passage or passages configured to carry a fluid. In such embodiment the fluid may comprise a thermal transfer fluid, or a lubricant. In the case where the fluid is a lubricant, in one embodiment the lubricant may form a fluid dynamic bearing for supporting the rotating shaft.

In another embodiment, one or more of the motor stators include cooling fins.

In a further embodiment, the rotating shaft comprises a segmented shaft, wherein the shaft segments are mechanically coupled to one another.

According to Aspect B, the present disclosure provides a fuel-cell-powered vehicle comprising the electrically-powered turbine assembly as above described, and one or more fuel cells and/or current inverters arranged outside of the electrically-powered turbine assembly.

In one embodiment of Aspect B, the air compressors are configured to deliver air to a cathode side of the one or more fuel cells.

In another embodiment of Aspect B, anode exhaust from the fuel cells is passed to the turbine.

In a further embodiment of Aspect B, the electric motor stators include fins configured to be cooled by airflow from the compressor.

In yet another embodiment of Aspect B, the system includes one or more inverters having cooling fins configured to extend into the housing and into cooling airflow from the compressor.

In a particularly preferred embodiment of Aspect B, the vehicle is an aircraft.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

Further features and advantages of the disclosure will be seen in the following detailed description, taken in conjunction with the accompanying drawings. The drawings described herein are for illustrative purposes only of selected embodiments and not all possible implementations and are not intended to limit the scope of the present disclosure.

In the drawings.

DETAILED DESCRIPTION

Figure 1:
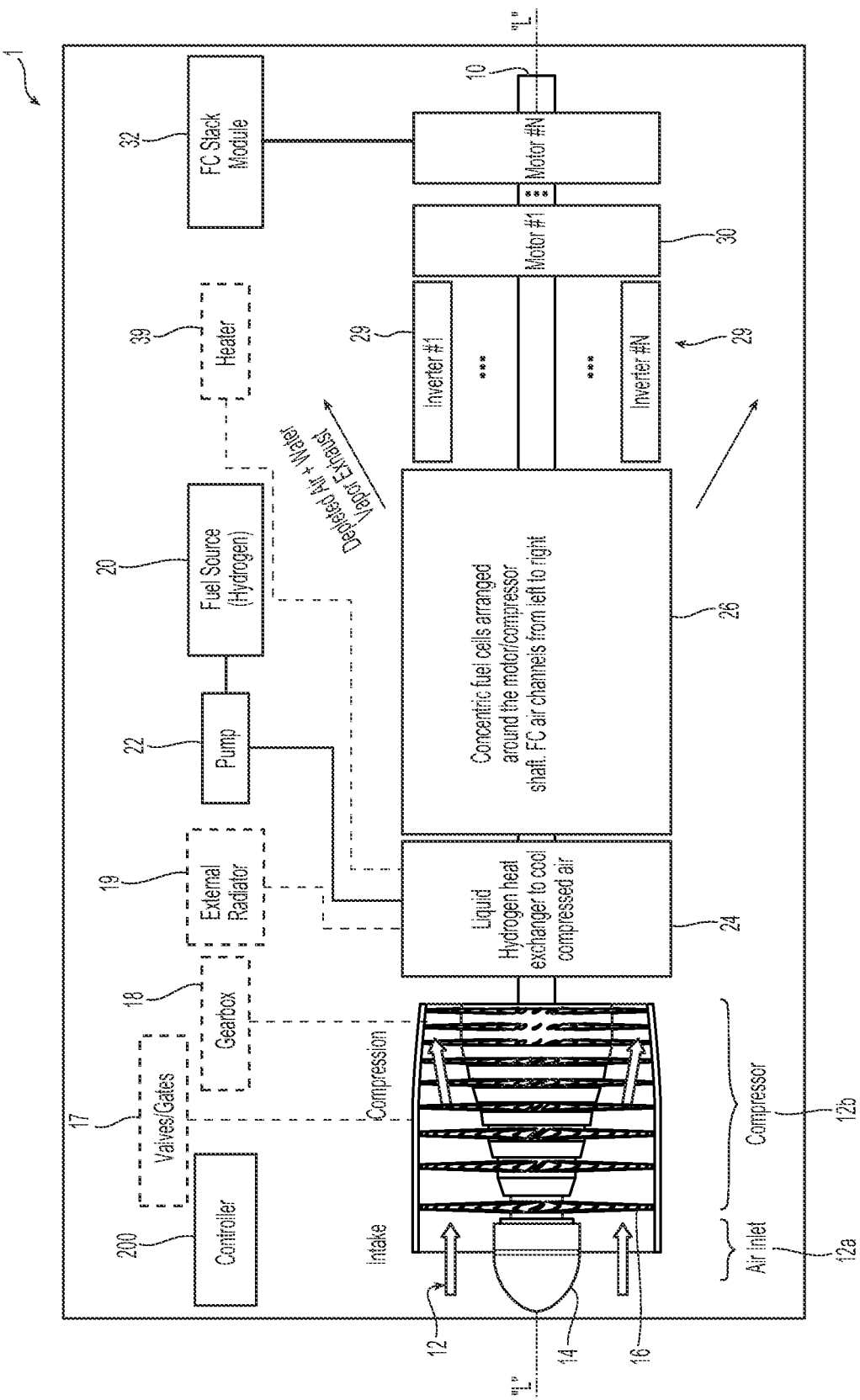
FIG. 1 is a schematic view of an integrated hydrogen-electric engine system in accordance with the prior art.

Example embodiments will now be described more fully with reference to the accompanying drawings. Example embodiments are provided so that this disclosure will be thorough and will fully convey the scope to those who are skilled in the art. Numerous specific details are set forth, such as examples of specific components, devices, and methods to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, components, and/or groups, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer, or section from another element, component region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 2:
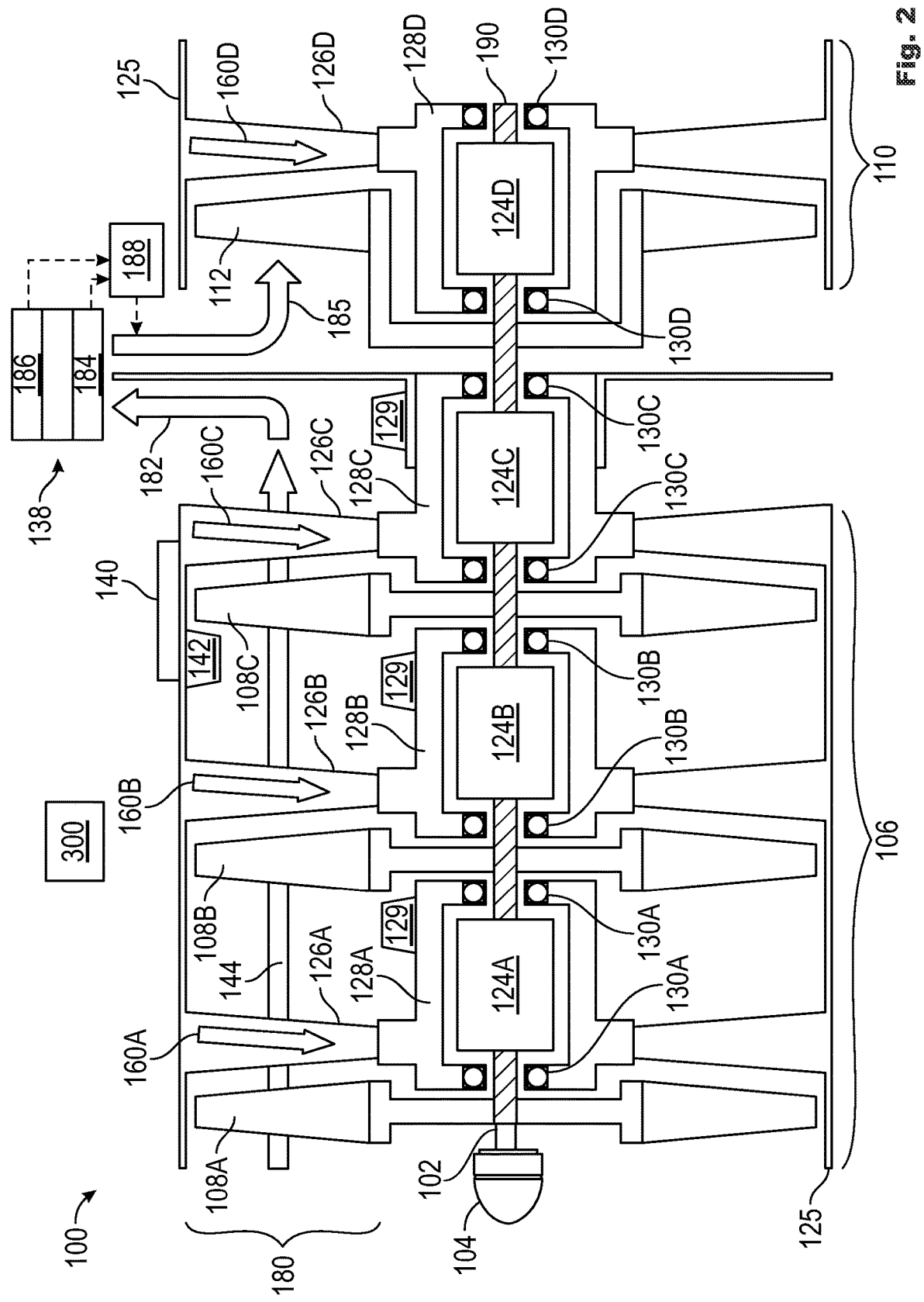
FIG. 2 is a schematic view of an integrated hydrogen-electric engine system in accordance with the present disclosure.

FIG. 2 illustrates an integrated hydrogen-electric engine system 100 that can be utilized, for example, in a turboprop or turbofan system in accordance with the present disclosure. Integrated hydrogen-electric engine system 100 includes an elongated shaft 102 that defines a longitudinal axis "L" and extends through the entire powertrain of integrated hydrogen-electric engine system 100 to function as a common shaft for the various components of the powertrain. Elongated shaft 102 supports a propulsor 104 (e.g., a fan or propeller) and a multi-stage air compressor section 106 comprising a plurality of compressor rotors 108A, 108B, 108C and a turbine section 110 comprising a turbine rotor 112. Compressor rotors 108A, 108B, 108C and turbine rotor 112 are fixed to rotating shaft 102. A plurality of electric motor cores 124A, 124B, 124C are also rotatably fixed to rotating shaft 102 within the multi-stage air compressor section 106, and an electric motor core 124D is fixed to rotating shaft 102 in turbine section 110. The air compressor motor housings 128A, 128B, 128C are supportably fixed to housing 125 on air compressor stators 126A, 126B, 126C. The turbine motor housing 128D is supportably fixed to housing 125 on turbine stator 126D. Electric motor housings 128A, 128B, 128C are affixed to air compressor stators 126A, 126B, 126C, and electric motor housing 128D is affixed to turbine stator 126D which in turn is fixed to housing 125. Electric motor housings 128A, 128B, 128C and 128D also form the stators for the electric motors. Shaft 102 is rotatably supported within compressor stators 126A, 126B, 126C and turbine stator 126D on bearing pairs 130A, 130B, 130C, 130D, respectively.

Compressor stators 126A, 126B, 126C, and turbine stator 126D include internal passages 160A, 160B, 160C, 160D for carrying coolant air to and from the electric motor cores 124A, 124B, 124C, 124D. Internal passages 160A, 160B, 160C, 160D also may be configured to deliver lubricant to bearings 130A, 130B, 130C, 130D. Compressor stators 126A, 126B, 126C and turbine stator 126D also may be configured for accommodating electrical wiring for carrying electricity generated by the fuel cells 138 (only one of which is shown, and not to scale) to power the electric motors. Alternatively, compressor or turbine stators 126A, 126B, 126C, 126D may be formed of electrically conductive materials for carrying electric current to the electric motors.

The integrated hydrogen-electric engine system 100 also includes inverter(s) 140 located immediately to the outside of housing 125 with the shortest path to each motor. Inverter(s) 140 may include cooling fin(s) 142 extending into housing 125 in contact with the compressor airflow 144. In similar manner, the electric motor stators 128A, 128B, 128C may include cooling fin(s) 129, and the compressor airflow also may be used to cool the electric motors. Inverter(s) 140 are configured to convert direct current from the fuel cells 138 to alternating current for actuating the one or more electric motor(s) in electrical communication with inverter(s) 140. The one or more electric motor(s) drives elongated shaft 102 which carries the compressor rotors 108A, 108B, 108C and propulsor 104.

In operation, air 144 is introduced into air inlet 180 and compressed by the air compressor section 106 and passed via high pressure air outlet 182 to the cathode side 184 of fuel cell 138 where the oxygen in the air is reacted with hydrogen to produce electricity and reaction exhaust comprising primarily hot air and hot water. The water is separated, and the hot air exhaust from the fuel cell 138 is passed via turbine inlet 185 to the turbine section 110 where it is used for driving the one or more turbine rotors 112. Optionally, the hydrogen exhaust from the fuel cell anode 186 can be combined with the exhaust from the fuel cell cathode 184 and combusted in an anode tail oxidizer (ATO) 188 before returning to the turbine inlet 185.

Integrated hydrogen-electric engine system 100 further includes a controller 300 for controlling the various aspects of the integrated hydrogen-electric engine system 100 and/or other components of the aircraft system. For example, controller 300 can be configured to manage a flow of liquid hydrogen, manage coolant liquids and rates of hydrogen and air going into the system and/or flows of hydrogen fuel and air to the fuel cells.

A feature and advantage of the instant disclosure is that the housing, compressor stators, electric motor stator and turbine stators each serve multiple functions. This results in fewer components being needed, and a corresponding weight reduction. Also packaging the electric motor cores within the compressor section and turbine section permits us to provide an extremely compact hydrogen fuel-cell-powered electric engine system providing high power density, which may be sized and shaped to fit within the existing conventional aircraft wing nacelle.

Various changes may be made in the foregoing disclosure without departing from the spirit and scope thereof. For example, fluids for cooling the electric motors and fluids for lubricating the shaft bearings may be piped in the passages 160A, 160B, 160C, 160D within the compressor stators 126A, 126B, 126C and the turbine stator 126D. The passages may enclose fluid flow tubes, or the passages may be hollow passages connecting the inner and outer ends of the stators. We also can include sensors and phase encoders (not shown) within the motor stators. Also, different stators may be connected to different phase leads of the electric motors.

The rotating shaft 102 may comprise a unitary shaft or segmented shaft in which the segments are mechanically connected together by splines, couplings, gears and/or clutches. Shaft(s) 102 also may be provided with passage(s) 190 for conveying fluids from one location along shaft to another. Seals and rotating couplings (not shown) can enable multiple fluids to be conveyed to and from multiple locations within the integrated hydrogen-electric engine system.

In one embodiment, the shaft 102 may be configured to carry cryogenic fluids, including, for example, liquid hydrogen from the fuel store, to the electric motors. This would enable us to employ superconducting motor windings. Yet other changes are possible.

Figure 3:
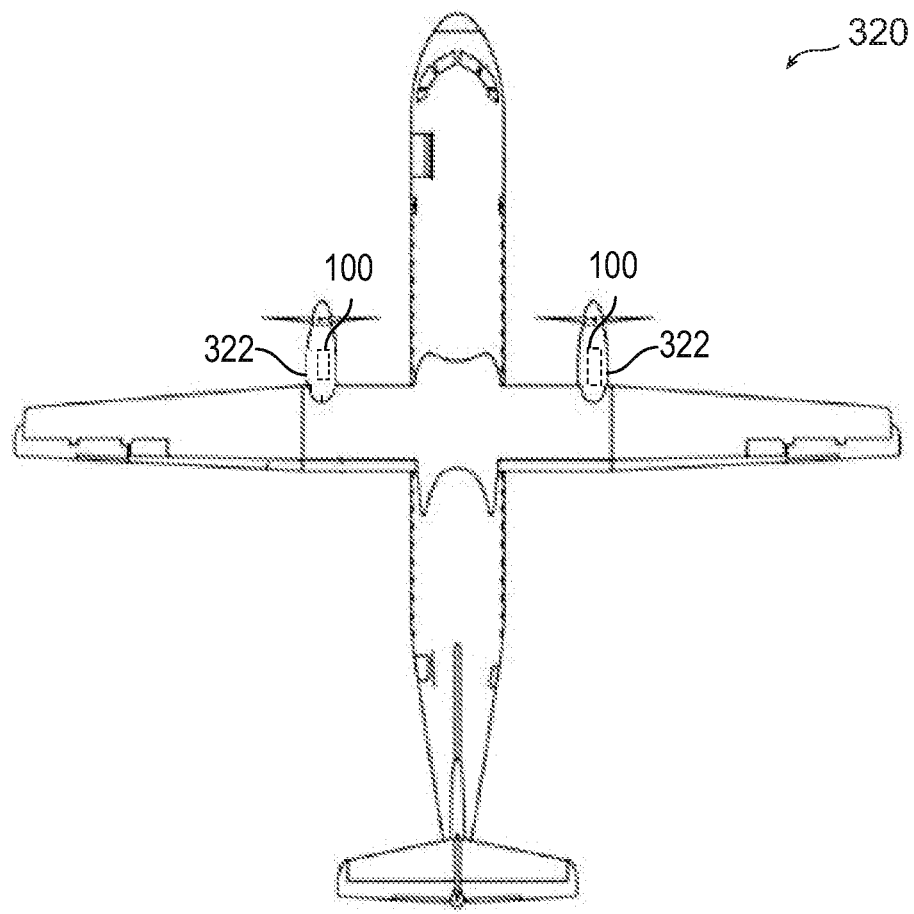
FIG. 3 is a schematic view of an aircraft incorporating a pair of hydrogen fuel cell electric engine systems in accordance with the present disclosure.

FIG. 3 illustrates an aircraft 320 including a pair of integrated hydrogen fuel cell electric engine systems 100 as above described in the wing nacelles 322 of an aircraft.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Various changes and advantages may be made in the above disclosure without departing from the spirit and scope thereof.

What is claimed:

1. A fuel-cell-powered vehicle comprising an electrically-powered turbine assembly comprising:
    a housing;
    a rotating shaft;
    an air compressor comprising a compressor stator fixed to the housing and a compressor rotor fixed to the rotating shaft;
    an electric motor including an electric motor stator fixed to the compressor stator, and an electric motor rotor fixed to the rotating shaft;
    a turbine including a turbine stator fixed to the housing, and a turbine rotor fixed to the rotating shaft, and
    one or more filet cells arranged around an outside of the electrically-powered turbine assembly, wherein anode exhaust from the one or more fuel cells is configured to be passed to the turbine.

2. The fuel-cell-powered vehicle of claim 1, wherein the compressor stator has a passage configured to carry a fluid.

3. The fuel-cell-powered vehicle of claim 2, wherein the fluid comprises a thermal transfer fluid.

4. The fuel-cell-powered vehicle of claim 1, wherein the fuel cell comprises a hydrogen fuel cell, wherein the rotating shaft is configured to carry liquid hydrogen to cool the electric motor windings.

5. A fuel-cell-powered vehicle comprising an electrically-powered turbine assembly comprising:
    a housing;
    a rotating shaft;
    an air compressor comprising a compressor stator fixed to the housing and a compressor rotor fixed to the rotating shaft;
    an electric motor including an electric motor stator fixed to the compressor stator, and an electric motor rotor fixed to the rotating shaft;
    a turbine including a turbine stator fixed to the housing, and a turbine rotor fixed to the rotating shaft;
    one or more fuel cells arranged around an outside of the electrically-powered turbine assembly; and
    one or more inverters electrically connected to the electric motors, wherein the one or more inverters include cooling fins extending into the housing and into cooling airflow from the air compressor.

6. The fuel-cell-powered vehicle of claim 5, wherein the air compressor is configured to deliver air to a cathode side of the one or more fuel cells.

7. The fuel-cell-powered vehicle of claim 5, wherein the electric motor stator includes fins configured to be cooled by airflow from the compressor.

8. The fuel-cell-powered vehicle of claim 5, wherein the vehicle is an aircraft.

9. The fuel-cell-powered vehicle of claim 5, wherein an electric motor or generator is affixed to the turbine stator, and a turbine rotor is fixed to the motor or generator rotor.

10. The fuel-cell-powered vehicle of claim 5, wherein the electric motor rotor, the compressor rotor, and the turbine rotor are mechanically linked together via the rotating shaft.

11. The fuel-cell-powered vehicle of claim 5, wherein the compressor stator is configured for carrying an electric current.

12. The fuel-cell-powered vehicle of claim 11, wherein the compressor stator has a passage configured to accommodate an electrical conduit within the compressor stator.

13. The fuel-cell-powered vehicle of claim 11, wherein the compressor stator is formed of an electrically conductive material and is configured to carry an electrical current.

14. The fuel-cell-powered vehicle of claim 5, wherein the compressor stator has a passage configured to carry a fluid.

15. The fuel-cell-powered vehicle of claim 14, wherein the fluid comprises a thermal transfer fluid.

16. The fuel-cell-powered vehicle of claim 14, wherein the fluid comprises a lubricant.

17. The fuel-cell-powered vehicle of claim 16, wherein the lubricant forms a fluid dynamic bearing for supporting the rotating shaft.

18. The fuel-cell-powered vehicle of claim 5, wherein the electric motor stator includes cooling fins.

19. The fuel-cell-powered vehicle of claim 5, wherein the rotating shaft comprises a segmented shaft, wherein the shaft segments are mechanically coupled to one another.

20. The fuel-cell-powered vehicle of claim 5; wherein the fuel cell comprises a hydrogen fuel cell, wherein the rotating shaft is configured to carry liquid hydrogen to cool the electric motor windings.

* * * * *